United States Patent [19]

Kato et al.

[11] Patent Number: 4,772,295
[45] Date of Patent: Sep. 20, 1988

[54] METHOD FOR RECOVERING HYDROCARBON VAPOR

[75] Inventors: Moritake Kato; Norio Inoue; Yoshiki Shibuya, all of Tokyo, Japan

[73] Assignee: Nippon Kokan Kabushiki Kaisha, Tokyo, Japan

[21] Appl. No.: 51,928

[22] Filed: May 19, 1987

[30] Foreign Application Priority Data

May 27, 1986 [JP] Japan .................. 61-120311
May 27, 1986 [JP] Japan .................. 61-120312

[51] Int. Cl.4 .................. B01D 53/14; B01D 53/22
[52] U.S. Cl. .................. 55/16; 55/88; 55/89; 585/819
[58] Field of Search .................. 55/16, 68, 88, 89; 585/818, 819

[56] References Cited

U.S. PATENT DOCUMENTS

| 2,159,434 | 5/1939 | Frey | 585/818 X |
|---|---|---|---|
| 2,617,493 | 11/1952 | Jones | 55/16 |
| 2,970,106 | 1/1961 | Binning et al. | 55/16 X |
| 3,534,528 | 10/1970 | Porter | 55/16 |
| 3,819,742 | 6/1974 | Brun et al. | 585/818 |
| 3,907,524 | 9/1975 | Haines, Jr. | 55/88 |
| 3,930,990 | 1/1976 | Brun et al. | 585/818 |
| 4,043,769 | 8/1977 | Nishino et al. | 55/25 |
| 4,066,423 | 1/1978 | McGill et al. | 55/88 X |
| 4,171,017 | 10/1979 | Klass | 55/16 X |
| 4,444,571 | 4/1984 | Matson | 55/16 |
| 4,466,946 | 8/1984 | Goddin, Jr. et al. | 55/16 X |
| 4,553,983 | 11/1985 | Baker | 55/16 |
| 4,591,365 | 5/1986 | Burr | 55/16 |
| 4,639,257 | 1/1987 | Duckett et al. | 55/16 |
| 4,659,343 | 4/1987 | Kelly | 55/16 |

FOREIGN PATENT DOCUMENTS

| 0121356 | 7/1984 | European Pat. Off. |
| 0247585 | 5/1987 | European Pat. Off. |
| 39785 | 7/1977 | Japan |

Primary Examiner—Robert Spitzer
Attorney, Agent, or Firm—Frishauf, Holtz, Goodman & Woodward

[57] ABSTRACT

A method for recovering hydrocarbon vapor wherein permeable mixed gases of high concentration hydrocarbon vapor and the residual mixed gases of low concentration hydrocarbon vapor are separated, through gas separation membrane, from initial mixed gases containing hydrocarbon vapor to absorb permeable mixed gases, and a method for recovering hydrocarbon vapor wherein initial mixed gases containing hydrocarbon vapor are brought into contact with liquid absorbent to recover hydrocarbon vapor, and gases of high concentration hydrocarbon vapor and gases of low concentration hydrocarbon vapor are separated, through gas separation membrane, from treated gases from which hydrocarbon vapor has been absorbed in the preceeding process.

23 Claims, 1 Drawing Sheet

METHOD FOR RECOVERING HYDROCARBON VAPOR

BACKGROUND OF THE INVENTION

1. Field of the Invention

The present invention relates to a method for recovering hydrocarbon vapor from mixed gases, and more particularly to a method for recovering hydrocarbon vapor to absorb hydrocarbon vapor by means of liquid absorbent.

2. Description of the Related Arts

Mixed gases containing hydrocarbon, which generates when a storage tank, a tank truck or a tank wagon is filled with volatile hydrocarbon liquid, for example, gasoline, kerosene and various classes of alcohol, have been conventionally left released to the air. Mixed gases containing hydrocarbon, which evaporates from a storage tank when air temperature rises, has also been emitted into the air. These emission gases are recognized as one of the most serious causes of air pollution as the substance forming photochemical smog. In some local governments exhausting concentration of hydrocarbon is regulated.

Among methods of recovering volatile hydrocarbon vapor from these mixed gases, there are absorption process, adhesion process and low temperature processing method. Generally, various absorption methods at normal temperature and pressure are mostly practiced.

Japanese Examined Patent Publication (KOKOKU) No. 39785/77, for example, discloses a method wherein:
  (a) Gasoline vapor is absorbed by a non-volatile organic liquid absorbent of petroleum at normal temperature;
  (b) The liquid absorbent is transferred to a recovering column, wherein the gasoline vapor is separated from the liquid absorbent at the pressure reduced to approximately 25 Torr by means of a vacuum pump, the liquid absorbent being recovered; and
  (c) The separated gasoline vapor is absorbed by liquid gasoline for recovery.

U.S. Pat. No. 4,043,769 describes another method wherein:
  (a) Mixed gases containing gasoline vapor is increased in pressure by a gas-compressor and a greater part of gasoline vapor is recovered through absorption thereof by liquid gasoline;
  (b) The gasoline vapor remaining in the mixed gases is absorbed in non-volatile organic liquid absorbent of petroleum;
  (c) Gasoline vapor is separated and recovered from the liquid absorbent at the pressure reduced to 125 Torr by means of a vacuum-pump; and
  (d) The gasoline vapor recovered in (c) is returned to the entrance of the gas-compressor.

Those above mentioned methods, however, are disadvantageous in that the absorption and recovery process is complicated. Consequently, the operation as well as the equipment system cannot be simplified. In other words, in addition to equipment for process of absorption and recovery by using liquid gasoline, an absorption column using non-volatile organic liquid of petroleum, a recovery column and auxiliaries for example, a circulation-pump and a vacuum-pump are required.

SUMMARY OF THE INVENTION

It is an object of the present invention to provide a method for recovering hydrocarbon vapor from mixed gases containing hydrocarbon vapor more economically by using more simplified equipment and process.

In accordance with the present invention, a method is provided to recover hydrocarbon vapor, which comprises the steps of:
  Separating permeable mixed gases of high concentration hydrocarbon vapor and residual mixed gases of low concentration hydrocarbon vapor, through gas separation membrane, from initial mixed gases containing hydrocarbon vapor; and
  bringing said permeable mixed gases of high concentration hydrocarbon vapor into contact with liquid absorbent in an absorption column to absorb hydrocarbon.

Furthermore, a method is provided for recovering hydrocarbon vapor which comprises the steps of:
  bringing initial mixed gases containing hydrocarbon vapor into contact with liquid absorbent in an absorption column to absorb hydrocarbon vapor;
  separating permeable mixed gases of high concentration hydrocarbon vapor and residual mixed gases of low concentration hydrocarbon vapor, through gas separation membrane, from treated mixed gases from which hydrocarbon vapor has been absorbed in the preceeding step; and
  returning said permeable mixed gases to be mixed with said initial mixed gases.

The other objects and advantages of the present invention will become apparent from the detail description to follow taken in conjunction with the drawings appended.

DESCRIPTION OF THE PREFERRED EMBODIMENT

Figure 1:
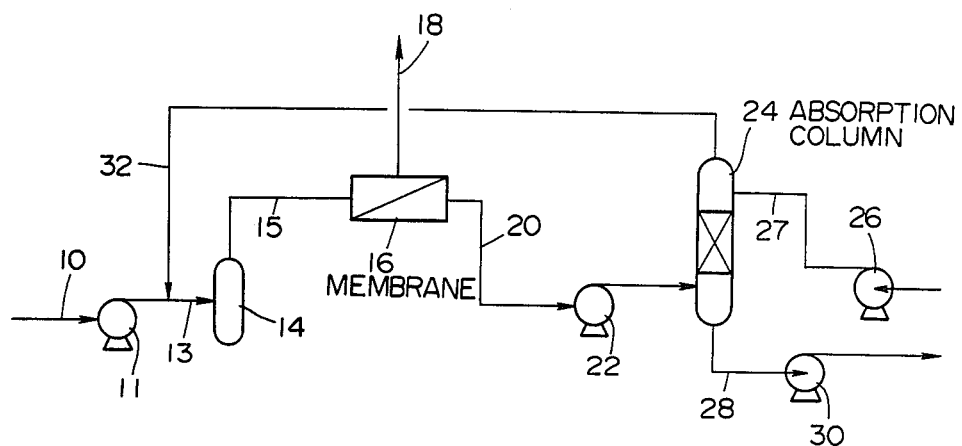
FIG. 1 is a schematic diagram showing an embodiment of equipment for a method for recovering hydrocarbon vapor according to the present invention.

The invention method can be used to recover various hydrocarbon vapors. The hydrocarbon vapors can be at least one selected from the group consisting of gasoline vapor, kerosene vapors, benzene vapors and alcohol vapors.

Referring to the drawings, a method for recovering hydrocarbon vapor will now be described.

FIG. 1 diagrammatically illustrates an embodiment of equipment according to the present invention. Initial mixed gases 10 containing hydrocarbon vapor is increased in pressure by blower 11, followed by being mixed with return gases 32, recycled from absorption column 24, which is specifically explained later. From these mixed gases 13 composed of the initial mixed gases and the return gases, mist and dust are removed by filter separator 14 to form clean mixed gases 15, which are sent to gas separation membrane 16.

That is to say, from the clean gases, hydrocarbon vapor having molecular weight comparatively large enough to permeate through the gas separation membrane are separated, while the residual gases 18 having hydrocarbon concentration of 5% or less by volume are released to the atmosphere. Permeable mixed gases 20 of high concentration hydrocarbon vapor, thus separated through the gas separation membrane, are drawn by vacuum-pump 22, subsequently increased in pressure and transferred to absorption column 24. In this embodiment, pressure of the suction side of the gas separation membrane is reduced to and kept at less than the atmospheric pressure (760 Torr). Liquid absorbent 27 is supplied by liquid absorbent supply pump 26 through the top of absorption column 24. Mixed permeable gases 20, introduced into the absorption column through the bottom of the absorption column, contacts directly with liquid absorbent 27, while the mixed permeable gases are ascending through fillers in the absorption column. In order to increase efficiency in recovering hydrocarbon vapor, the operation in the absorption column is recommended to be carried out at a pressure of slightly higher than the atmospheric pressure (760 Torr), since mixed permeable gases 20 contain air. Liquid absorbent 28 having absorbed hydrocarbon vapor is returned to liquid absorption tank by return-pump 30. Return gases 32 containing slightly hydrocarbon vapor, is returned to the point just before filter separator 14 to be recycled. In this embodiment, if a pressure of mixed gas is raised up to a level of several kg/cm$^2$.G by a gas-compressor in place of blower 11, a pressure of mixed permeable gases 20, separated through gas separation membrane 16, is raised to a level of the atmospheric pressure (760 Torr) or more and return gases 32 are returned to the suction side of the gas compressor, then, equipment for the embodiment can be simplified since vacuum-pump 22 is not required. As gas separation membrane 16, those having permeability of hydrocarbon vapor in speed larger than that of air, for example, silicone rubber, acrylonitrile-butadiene or polyvinyl chloride substance are preferable.

The present invention will be understood more readily with the following examples; however, these examples are intended to illustrate the present invention and are not to be construed as limiting the scope thereof.

EXAMPLE 1

In this operation of an example of the present invention, initial mixed gases 10 consisted of 35% gasoline vapor and 65% air by volume.

The initial mixed gases of 400 Nm$^3$/H and return gases 32, recycled from absorption column 24, of 50 Nm$^3$H were mixed to form mixed gases 13 of 450 Nm$^3$/H. From mixed gases 13, mist and dust were removed through filter separator 14, and the mixed gases became clean mixed gases 15. From the clean mixed gases, hydrocarbon vapor was separated through gas separation membrane 16, and residual gases 18, having hydrocarbon concentration of 5% or less by volume, were released to the air. Mixed permeable gases 20, thus having passed through the gas separation membrane, of approximately 80% concentration hydrocarbon vapor, were sucked in by vacuum-pump 22 at a pressure of about 44 mm/Hg, subsequently increased in pressure and introduced into absorption column 24. The permeable mixed gases ascended through fillers in the absorption column wherein the operation was carried out at a pressure of 1 kg/cm$^3$ G. During the ascend, the permeable mixed gases contacted with liquid gasoline, as liquid absorbent, supplied into the absorption column through the top of the absorption column. The gases contained about 14% gasoline vapor, which was not absorbed. The gases, as return gases 32, were to be mixed with the initial mixed gases for recycling. In this example, gases of explosive nature, although used in the operation, were quite successfully treated at the normal pressure.

Figure 2:
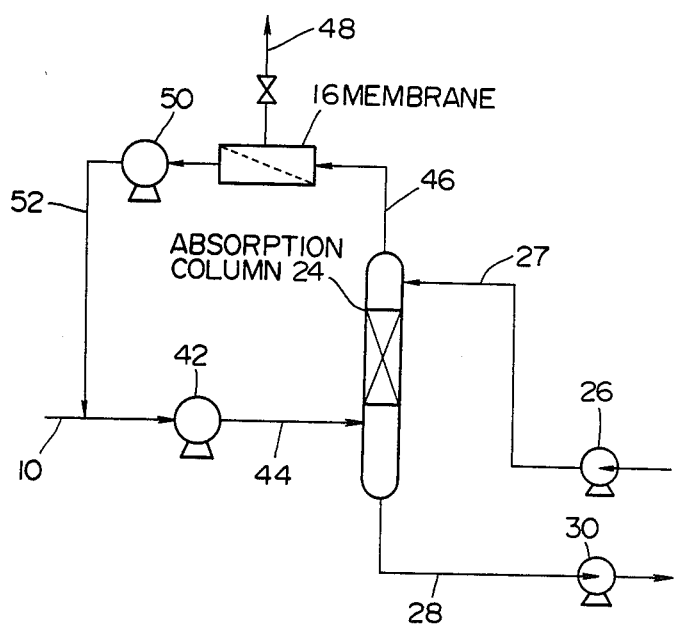
FIG. 2 is a schematic diagram showing another embodiment for a method for recovering hydrocarbon vapor according to the present invention.

Secondly, with reference specifically to the FIG. 2 of the drawing, another example of a method for recovering hydrocarbon vapor according to the present invention will now be described.

Initial mixed gases 10 together with return gases 52, which described later, were increased in pressure to 2 to 3 kg/cm$^2$ by means of gas compressor 42 and conveyed to absorption column 24. Liquid absorbent 27 is supplied through the top of the absorption column. Mixed gases 44 introduced through the bottom of the absorption column, contact directly with liquid absorbent 27, while ascending within the absorption column. Hydrocarbon vapor contained in mixed gases 44 is absorbed in the liquid absorbent. The liquid absorbent, having absorbed thus hydrocarbon vapor, stays at the bottom of the absorption column and is returned to a liquid absorbent tank by return-pump 30. Treated mixed gases 46 drawn out through the top of absorption column 24 is conveyed to gas separation membrane 16, since treated mixed gases 46 contain 10% or more hydrocarbon vapor. Hydrocarbon vapor contained in treated mixed gases 46 is passed through gas separation membrane 16 by means of reducing to 150 Torr the pressure on the suction side of the gas separation membrane, being transferred, as return gas 52, to be mixed together with initial mixed gases 10. Hydrocarbon vapor is preferentially passed through the gas separation membrane, and the discharge residual gases 48 whose concentration of hydrocarbon vapor has been reduced to 5% or less, is released to the air. The return gases having passed through the gas separation membrane are sucked by vacuum-pump 50, increased in pressure on the suction side and, furthermore, compressed by gas-compressor 50.

EXAMPLE 2

In this operation of another example of the present invention, initial gases 10 consisted of 35% gasoline vapor and 65% of air by volume.

The initial gases of 400 Nm$^3$/H and return gases 52 of 40 Nm$^3$/H were mixed. The mixed gases of 440 Nm$^3$/H were increased to a pressure of 2.5kg/cm$^2$ G by gas-compressor 42 and conveyed to absorption column 24. In the absorption column, mixed gas 44 contacted directly with liquid gasoline as liquid absorbent 27 supplied through the top of the absorption column, and gasoline vapor contained in mixed gases 44 was recovered in the state of the liquid gasoline. The liquid gasoline was returned to a gasoline tank by means of return-pump 30. Mixed gases 46 drawn out of the absorption column contained 12% gasoline vapor and were transferred to gas separation membrane 16, composed of silicone rubber substance. Gasoline vapor was selectively passed through the gas separation membrane to the suction side thereof to form mixed gases of 45% hydrocarbon vapor by volume. The mixed gases, as return gases 52, were transferred, by vacuum pump 50, to be mixed with the initial mixed gases. In this example, 85% or more of gasoline vapor was successfully recovered from initial mixed gases containing gasoline vapor.

As explained in Examples 1 and 2, the present invention enables hydrocarbon vapor to efficiently be separated and recovered from mixed gases containing hydrocarbon vapor. This method simplifies effectively equipment system as well as process of absorption and recovery and, thus, contributes greatly to commercial production.

What is claimed is:

1. A method for recovering hydrocarbon vapor from initial mixed gases containing hydrocarbon vapor, which comprises the steps of:
    separating the inital mixed gases into permeable mixed gases of high concentration hydrocarbon vapor and residual mixed gases of low concentration hydrocarbon vapor, with a gas separation membrane having an inlet side and a pass-out side,; and
    bringing said permeable mixed gases of high concentration hydrocarbon vapor into contact with liquid absorbent in an adsorption column to absorb hydrocarbon vapor therefrom, leaving unabsorbed return gases.

2. The method according to claim 1, further comprising the additional step of mixing the return gases containing hydrocarbon vapor which has not been absorbed in said liquid absorbent, with said initial mixed gases, thereby said return gases being recycled.

3. The method according to claim 1, further comprising the additional step of removing mist and dust from said initial mixed gases with a filter separator before the separating step.

4. The method according to claim 1, further comprising the additional step of releasing said residual gases to the air.

5. The method according to claim 1, wherein said initial mixed gases include mixed gases of air and hydrocarbon vapor.

6. The method according to claim 1, wherein said hydrocarbon vapor contained in said initial mixed gases are at least one selected from the group consisting of gasoline vapor, kerosene vapor, benzene vapor and alcohol vapor.

7. The method according to claim 1, wherein said step of separating permeable mixed gases comprises passing the mixed gases through a gas separation membrane while maintaining a pressure at the pass-out side of said gas separation membrane of atmospheric pressure (760 Torr) or less.

8. The method according to claim 1, wherein said step of separating permeable mixed gases with a gas separation membrane includes increasing pressure of said permeable mixed gases before passing through said gas separation membrane and maintaining a pressure at the pass-out side of said gas separation membrane at atmospheric pressure (760 Torr) or more.

9. The method according to claim 1, wherein said gas separation membrane is at least one selected from the group consisting of silicone, acrylonitrile-butadiene and polyvinyl chloride.

10. The method according to claim 1, wherein said step of absorbing hydrocarbon vapor includes a step of bringing said permeable gases, introduced into the absorption column through the bottom of the absorption column, into contact with said liquid absorbent, supplied into the absorption column through the top of the absorption column.

11. The method according to claim 1, wherein said liquid absorbent is a liquid hydrocarbon.

12. The method according to claim 11, wherein said liquid hydrocarbon is at least one selected from the group consisting of liquid gasoline, liquid kerosene, liquid benzene and liquid alcohol.

13. A method for recovering hydrocarbon vapor which comprises the steps of:
    bringing initial mixed gases containing hydrocarbon vapor into contact with liquid absorbent in an absorption column to absorb hydrocarbon vapor and leaving unabsorbed treated mixed gases;
    separating the treated mixed gases into permeable mixed gases of high concentration hydrocarbon vapor and residual mixed gases of low concentration hydrocarbon vapor, with a gas separation membrane having an inlet and a pass-out side; and
    returning said permeable mixed gases to be mixed with said initial mixed gases.

14. The method according to claim 13, further comprising the additional step of releasing said residual mixed gases of low concentration hydrocarbon vapor.

15. The method according to claim 13, wherein said initial mixed gases include mixed gases of air and hydrocarbon vapor.

16. The method according to claim 13, wherein said hydrocarbon vapor is at least one selected from the group consisting of gasoline vapor, kerosene vapor, benzene vapor and alcohol vapor.

17. The method according to claim 13, wherein said step of separating permeable mixed gases of hydrocarbon vapor includes maintaining a pressure at the pass-out side of said gas separation membrane of atmospheric pressure (760 Torr) or less.

18. The method according to claim 13, wherein said gas separation membrane is at least one selected from the group consisting of silicone, acrylonitrile-butadiene and polyvinyl chloride.

19. The method according to claim 13, wherein said step of absorbing hydrocarbon vapor includes bringing said permeable mixed gases, introduced into the absorption column through the bottom of the absorption column, into contact with said liquid absorbent, supplied into the absorption column through the top of the absorption column.

20. The method according to claim 13, wherein said liquid absorbent is a liquid hydrocarbon.

21. The method according to claim 20, wherein said liquid hydrocarbon is at least one selected from the group consisting of gasoline liquid, kerosene liquid, benzene liquid and alcohol liquid.

22. A method for recovering hydrocarbon vapor from initial mixed gases containing hydrocarbon vapor comprising separating the initial mixed gases into permeable mixed gases of high concentration hydrocarbon vapor and residual mixed gases of low concentration hydrocarbon vapor with a separation membrane; and bringing said permeable mixed gases into contact with a liquid absorbent to absorb hydrocarbon vapors from said permeable mixed gases.

23. A method for recovering hydrocarbon vapor from initial mixed gases containing hydrocarbon vapor comprising bringing said initial mixed gases into contact with a liquid absorbent to absorb hydrocarbon vapors therefrom to form treated mixed gases; separating the treated mixed gases into permeable mixed gases of high concentration hydrocarbon vapor and residual mixed gases of low concentration hydrocarbon vapor with a separation membrane; and returning the permeable mixed gases to be mixed with the initial mixed gases.

* * * * *